US011771670B2

(12) United States Patent
Hotta et al.

(10) Patent No.: US 11,771,670 B2
(45) Date of Patent: Oct. 3, 2023

(54) REFINED CHLOROGENIC ACID-CONTAINING COMPOSITION MANUFACTURING METHOD

(71) Applicant: KAO CORPORATION, Tokyo (JP)

(72) Inventors: Yusuke Hotta, Kashima (JP); Yukiteru Sugiyama, Narita (JP)

(73) Assignee: KAO CORPORATION, Tokyo (JP)

( * ) Notice: Subject to any disclaimer, the term of this patent is extended or adjusted under 35 U.S.C. 154(b) by 379 days.

(21) Appl. No.: 16/345,194

(22) PCT Filed: Sep. 28, 2017

(86) PCT No.: PCT/JP2017/035267
§ 371 (c)(1),
(2) Date: Apr. 25, 2019

(87) PCT Pub. No.: WO2018/079178
PCT Pub. Date: May 3, 2018

(65) Prior Publication Data
US 2019/0274985 A1 Sep. 12, 2019

(30) Foreign Application Priority Data
Oct. 26, 2016 (JP) ................. 2016-209198

(51) Int. Cl.
A61K 36/00 (2006.01)
A61K 31/194 (2006.01)
A23L 33/105 (2016.01)
A61K 31/522 (2006.01)
A23F 5/00 (2006.01)
A61K 36/74 (2006.01)
A61P 9/12 (2006.01)
C07C 67/56 (2006.01)
A61P 1/16 (2006.01)
A61K 31/216 (2006.01)
A61P 39/06 (2006.01)
C07C 69/732 (2006.01)

(52) U.S. Cl.
CPC .............. *A61K 31/194* (2013.01); *A23F 5/00* (2013.01); *A23L 33/105* (2016.08); *A61K 31/216* (2013.01); *A61K 31/522* (2013.01); *A61K 36/74* (2013.01); *A61P 1/16* (2018.01); *A61P 9/12* (2018.01); *A61P 39/06* (2018.01); *C07C 67/56* (2013.01); *C07C 69/732* (2013.01); *A23V 2002/00* (2013.01)

(58) Field of Classification Search
CPC ....... A61K 31/194; A23L 33/105; A23F 5/02; A23F 5/10; A23F 5/24
See application file for complete search history.

(56) References Cited

U.S. PATENT DOCUMENTS

| | | | |
|---|---|---|---|
| 4,048,345 A | 9/1977 | Katz | |
| 4,481,223 A | 11/1984 | Hinman et al. | |
| 5,702,747 A | 12/1997 | Sipos et al. | |
| 9,029,588 B2 | 5/2015 | Yamawaki et al. | |
| 9,034,410 B2 | 5/2015 | Vella et al. | |
| 2006/0210689 A1 | 9/2006 | Velissariou et al. | |
| 2008/0044539 A1 | 2/2008 | Perlman et al. | |
| 2009/0053381 A1 | 2/2009 | Fukuda et al. | |
| 2009/0092736 A1 | 4/2009 | Koyama et al. | |
| 2012/0251678 A1 | 10/2012 | Leloup et al. | |
| 2013/0131165 A1 | 5/2013 | Sugiyama et al. | |
| 2013/0230608 A1 | 9/2013 | Silber et al. | |
| 2014/0135391 A1 | 5/2014 | Yamawaki et al. | |
| 2014/0271988 A1 | 9/2014 | Robinson et al. | |
| 2017/0013857 A1 | 1/2017 | Ozato | |
| 2018/0160696 A1 | 6/2018 | Ozato et al. | |
| 2019/0274985 A1 | 9/2019 | Hotta et al. | |

FOREIGN PATENT DOCUMENTS

| | | | |
|---|---|---|---|
| CN | 101133015 A | 2/2008 | |
| EP | 0666033 A1 * | 8/1995 | ............ A23F 5/223 |
| EP | 0916267 A2 | 5/1999 | |
| EP | 2592064 A1 | 5/2013 | |
| EP | 2644036 A1 | 10/2013 | |
| GB | 1488340 A | 10/1977 | |
| JP | 60-102143 A | 6/1985 | |
| JP | 2006-104070 A | 4/2006 | |
| JP | 2006-174746 A | 7/2006 | |
| JP | 2008-31150 A | 2/2008 | |
| JP | 2008-266144 A | 11/2008 | |
| JP | 2010-178664 A | 8/2010 | |
| JP | 2010-233485 A | 10/2010 | |
| JP | 2011-182749 A | 9/2011 | |
| JP | 2012-31165 A | 2/2012 | |
| JP | 5214518 B2 * | 6/2013 | |

(Continued)

OTHER PUBLICATIONS

Extended European Search Report dated Jun. 9, 2020, for European Application No. 17864962.0.

(Continued)

*Primary Examiner* — Qiuwen Mi

(74) *Attorney, Agent, or Firm* — Birch, Stewart, Kolasch & Birch, LLP

(57) ABSTRACT

Provided is a method of producing a purified chlorogenic acid-containing composition, including a contact step of bringing a chlorogenic acid-containing composition having solids concentration of from 1.5 mass % to 4.7 mass % and a "caffeine/chlorogenic acid" mass ratio of 5 or less into contact with a porous adsorbent.

16 Claims, No Drawings

(56) References Cited

FOREIGN PATENT DOCUMENTS

| | | |
|---|---|---|
| JP | 2013-138631 A | 7/2013 |
| JP | 2015-142565 A | 8/2015 |
| JP | 2016-47814 A | 4/2016 |
| JP | 2016-106627 A | 6/2016 |
| JP | 6389940 B2 | 9/2018 |
| JP | 2019-99 A | 1/2019 |
| JP | 2019-112466 A | 7/2019 |
| JP | 2019-112467 A | 7/2019 |
| JP | 6763841 B2 | 9/2020 |
| WO | WO 2007/122796 A1 | 11/2007 |
| WO | WO 2012/005293 A1 | 1/2012 |
| WO | WO 2014/155746 A1 | 10/2014 |
| WO | WO 2015/093522 A1 | 6/2015 |
| WO | WO 2016/031625 A1 | 3/2016 |

OTHER PUBLICATIONS

Author Unknown, "Carbohydrates in Coffee", URL: https:www.coffeechemistry.com/chemistry/carbohydrates/carbohydrates-in-coffee, XP055676898, Apr. 23, 2015, 5 pages.

Extended European Search Report, dated Mar. 23, 2020, for European Application No. 17863734.4.
Extended European Search Report, dated Mar. 25, 2020, for European Application No. 17865450.5.
U.S. Office Action for U.S. Appl. No. 16/345,188, dated Jan. 17, 2020.
U.S. Office Action for U.S. Appl. No. 16/345,188, dated Aug. 22, 2019.
International Search Report, dated Jan. 9, 2018, for International Application No. PCT/JP2017/035266, with an English translation.
International Search Report, dated Jan. 9, 2018, for International Application No. PCT/JP2017/035268, with an English translation.
Japanese Office Action, dated Apr. 6, 2018, for Japanese Application No. 2017-188160 with an English machine translation.
U.S. Office Action, dated Dec. 4, 2019, for U.S. Appl. No. 16/345,118.
International Search Report for PCT/JP2017/035267 (PCT/ISA/210) dated Jan. 9, 2018.
SUGI Blog, Sep. 6, 2014, retrived on Dec. 20, 2017, (https://ameblo.jp/sugichan0826/entry-11920899630.html) non-official translation (An Look at the ATAGO BRIX/TDS Scale), total of 7 pages.

* cited by examiner

REFINED CHLOROGENIC ACID-CONTAINING COMPOSITION MANUFACTURING METHOD

FIELD OF THE INVENTION

The present invention relates to a method of producing a purified chlorogenic acid-containing composition.

BACKGROUND OF THE INVENTION

As materials having bioactive functions, there have been proposed a variety of materials. For example, there are given polyphenols as those having bioactive functions, such as an antioxidative effect, an antihypertensive effect, and a hepatic function-improving effect. A chlorogenic acid, which is one of the polyphenols, has been reported to have a high antihypertensive effect, and is expected to find applications in supplements and food and drink.

As a material containing a large amount of the chlorogenic acid, there are given coffee beans. A chlorogenic acid-containing composition obtained by extracting the coffee beans contains caffeine as a component other than the chlorogenic acid. As a method of removing caffeine from the chlorogenic acid-containing composition, there has been conventionally proposed a method involving concentrating an extract of green or roasted coffee beans to a refractive sugar content (20° C.) of from B×8° to B×60° as solids concentration, and then bringing the concentrated extract into contact with acid clay and/or activated clay (Patent Document 1).

(Patent Document 1) JP-A-2008-266144

SUMMARY OF THE INVENTION

The present invention provides a method of producing a purified chlorogenic acid-containing composition, comprising a contact step of bringing a chlorogenic acid-containing composition having solids concentration of from 1.5 mass % to 4.7 mass % and a mass ratio of caffeine/chlorogenic acid of 5 or less into contact with a porous adsorbent.

DETAILED DESCRIPTION OF THE INVENTION

When a chlorogenic acid-containing composition is brought into contact with a porous adsorbent, such as activated carbon or clay, the porous adsorbent adsorbs and removes not only caffeine, but also a chlorogenic acid. In addition, as the treated solids amount of the chlorogenic acid-containing material increases with respect to the porous adsorbent, the caffeine-removing capacity of the porous adsorbent reduces. Accordingly, the treatable solids amount of the chlorogenic acid-containing material is limited with respect to a unit amount of the porous adsorbent.

Therefore, the present invention relates to a method of producing a purified chlorogenic acid-containing composition in which the caffeine-selective removing property of a porous adsorbent is enhanced, and in which the treatable solids amount of a chlorogenic acid-containing material is increased with respect to a unit amount of the porous adsorbent.

The inventors of the present invention made various investigations. As a result of the investigations, they found that the above-mentioned problem can be solved by controlling solids concentration and a "caffeine/chlorogenic acid" mass ratio.

According to the present invention, through a simple operation, the caffeine-selective removing property of the porous adsorbent can be enhanced, and the treatable solids amount of the chlorogenic acid-containing material can be increased with respect to a unit amount of the porous adsorbent.

Hereinafter, a method of producing a purified chlorogenic acid-containing composition of the present invention is described. The term "chlorogenic acid" as used herein is a collective term for monocaffeoylquinic acids including 3-caffeoylquinic acid, 4-caffeoylquinic acid, and 5-caffeoylquinic acid, and monoferuloylquinic acids including 3-feruloylquinic acid, 4-feruloylquinic acid, and 5-feruloylquinic acid. The content of the chlorogenic acid is defined based on the total amount of the six of chlorogenic acids.

[Chlorogenic Acid-Containing Composition]

In the present invention, a chlorogenic acid-containing composition to be brought into contact with a porous adsorbent has solids concentration of from 1.5 mass % to 4.7 mass %, and the solids concentration is preferably 4.5 mass % or less, more preferably 4.0 mass % or less, even more preferably 3.5 mass % or less, from the viewpoints of the caffeine-selective removing property and the treatable solids amount with respect to a unit weight of the porous adsorbent. In addition, the solids concentration is preferably 1.6 mass % or more, more preferably 1.7% or more, from the viewpoint of a reduction in concentration load on the purified chlorogenic acid-containing composition obtained by the present invention. Such solids concentration falls within the range of preferably from 1.5 mass % to 4.5 mass %, more preferably from 1.6 mass % to 4.0 mass %, even more preferably from 1.7 mass % to 3.5 mass %. The term "solids" as used herein refers to a residue obtained by drying a sample in an electric thermostat dryer at 105° C. for 3 hours to remove volatile substances.

In the present invention, the chlorogenic acid-containing composition to be brought into contact with the porous adsorbent has a "caffeine/chlorogenic acid" mass ratio of 5 or less, and the "caffeine/chlorogenic acid" mass ratio is preferably 0.001 or more, more preferably 0.005 or more, even more preferably 0.01 or more, and is preferably 2.5 or less, more preferably 1 or less, even more preferably 0.4 or less, from the viewpoint of the treatable solids amount of the chlorogenic acid-containing material with respect to a unit amount of the porous adsorbent. Such "caffeine/chlorogenic acid" mass ratio falls within the range of preferably from 0.001 to 2.5, more preferably from 0.005 to 1, even more preferably from 0.01 to 0.4.

In addition, the chlorogenic acid-containing composition may be in any of various forms, such as a liquid, a slurry, a semisolid, and a solid.

In the present invention, as the chlorogenic acid-containing composition to be brought into contact with the porous adsorbent, there may be used a chlorogenic acid-containing composition obtained by adjusting an extract extracted from coffee beans by an appropriate method or a commercially available chlorogenic acid preparation so as to achieve solids concentration and "caffeine/chlorogenic acid" mass ratio of the above-mentioned predetermined values. Of those, a chlorogenic acid-containing composition obtained by subjecting coffee beans to column extraction using an aqueous solvent is preferred. The coffee beans and extraction method to be used for obtaining a chlorogenic acid-containing composition suitable in the present invention are described below.

(Coffee Beans)

The coffee beans are preferably at least one selected from the group consisting of green coffee beans, decaffeinated green coffee beans, roasted coffee beans having an L value of 30 or more, and decaffeinated roasted coffee beans having an L value of 25 or more, from the viewpoint of the ease with which the "caffeine/chlorogenic acid" mass ratio of the extract is controlled. As used herein, the term "decaffeinated green coffee beans" refers to coffee beans obtained by subjecting green coffee beans to decaffeination treatment, the term "roasted coffee beans having an L value of 30 or more" refers to coffee beans obtained by subjecting green coffee beans to roasting treatment so as to have an L value of 30 or more, and the term "decaffeinated roasted coffee beans having an L value of 25 or more" refers to coffee beans obtained by subjecting decaffeinated green coffee beans to roasting treatment so as to have an L value of 25 or more. Of those, as the coffee beans, green coffee beans are preferred from the standpoint of the content of the chlorogenic acid.

The L value of the roasted coffee beans is preferably 33 or more and less than 65, more preferably 36 or more and less than 65, more preferably 40 or more and less than 65, more preferably 45 or more and less than 65, more preferably 53 or more and less than 65, more preferably from 55 to 60, even more preferably from 55 to 58. In addition, the L value of the decaffeinated roasted coffee beans is preferably 25 or more and less than 50, more preferably from 30 to 45, even more preferably from 33 to 40. The term "L value" as used herein refers to a value as determined by measuring the lightness of roasted coffee beans with a colorimeter under the assumption that black has an L value of 0 and white has an L value of 100. The roasted coffee beans to be subjected to the measurement are ground to an average particle size of 0.3 mm.

The bean species of the coffee beans may be, for example, any one of *Arabica, Robusta, Liberica*, and *Arabusta*. In addition, the producing region of the coffee beans is not particularly limited, and examples thereof include Brazil, Colombia, Tanzania, Mocha, Kilimanjaro, Mandheling, Blue Mountain, Guatemala, and Vietnam.

As a method of subjecting the green coffee beans to the decaffeination treatment, a known method may be adopted, and examples thereof may include a Swiss Water method, a supercritical carbon dioxide extraction method, and an organic solvent extraction method. Of those, a Swiss Water method or a supercritical carbon dioxide extraction method is preferred from the viewpoint of a reduction in turbidity of the extract.

(Extraction)

A known method, such as column extraction or batch extraction, may be adopted as the extraction method. Of those, column extraction is preferred from the viewpoint of a reduction in turbidity of the extract.

The column extractor is not particularly limited as long as the column extractor comprises, for example, a supply port for an aqueous solvent and a discharge port for an extract solution. A column extractor comprising the following is suitably used: a supply valve for supplying the aqueous solvent and a discharge valve for discharging the extract solution, which are arranged in the lower part of the extractor; a shower nozzle for supplying the aqueous solvent, which is arranged in the upper part; and a retainer plate for retaining the coffee beans, which is arranged inside the extractor. The retainer plate is not particularly limited as long as the coffee beans and the extract solution can be separated from each other. Examples thereof may include a mesh and a punched metal. As the shape of the retainer plate, there are given, for example, a flat plate shape, a conical shape, and a pyramidal shape. In addition, the opening size of the retainer plate is not particularly limited as long as the opening size is smaller than the average particle size of the coffee beans, and may be appropriately selected.

In addition, as a method of loading the column extractor with the coffee beans, it is appropriate to put the coffee beans into the column extractor. When two or more of coffee beans are used, the column extractor may be loaded with a mixture of the two or more of coffee beans, or may be loaded with layers of the respective kinds of coffee beans.

Examples of the aqueous solvent include water, a water-soluble organic solvent, water-soluble organic solvent-containing water, milk, and carbonated water. Examples of the water-soluble organic solvent include an alcohol, a ketone, and an ester. In consideration of use in foods, an alcohol is preferred, and ethanol is more preferred. The concentration of the water-soluble organic solvent in the water-soluble organic solvent-containing water may be appropriately selected. Of those, as the aqueous solvent, water is preferred. Examples of the water include tap water, natural water, distilled water, and ion-exchanged water. Of those, ion-exchanged water is preferred in terms of taste.

In addition, the pH (20° C.) of the aqueous solvent is generally from 4 to 10, and is preferably from 5 to 7 from the viewpoint of taste and flavor. In order to adjust a pH to the desired one, the pH may be adjusted by adding a pH adjuster into the aqueous solvent. Examples of the pH adjuster include sodium hydrogen bicarbonate, sodium hydrogen carbonate, L-ascorbic acid, and sodium L-ascorbate.

The temperature of the aqueous solvent is preferably 75° C. or more, more preferably 77° C. or more, even more preferably 79° C. or more, from the viewpoint of an increase in recovery rate of the chlorogenic acid, and is preferably 98° C. or less, more preferably 95° C. or less, even more preferably 89° C. or less, from the viewpoint of a reduction in turbidity. The temperature of the aqueous solvent falls within the range of preferably from 75° C. to 98° C., more preferably from 77° C. to 95° C., even more preferably from 79° C. to 89° C.

The aqueous solvent may be supplied from the lower part of the column extractor toward the upper part thereof (upflow), or from the upper part of the column extractor toward the lower part thereof (downflow). In addition, the following may be performed: the aqueous solvent is supplied in a predetermined amount from the lower part of the column extractor and the supply is stopped, and then the aqueous solvent is supplied from the shower nozzle in the upper part, and simultaneously, the extract solution is discharged from the lower part. In this case, the supply amount of the aqueous solvent from the lower part may be appropriately set, and is preferably such an amount that part of the coffee beans in the column extractor can be immersed in the aqueous solvent.

The feeding amount of the aqueous solvent in terms of bed volume (BV) with respect to the mass of the coffee beans is preferably 1 (w/w) or more, more preferably 2 (w/w) or more, even more preferably 3 (w/w) or more, from the viewpoint of an increase in recovery rate of the chlorogenic acid, and is preferably 30 (w/w) or less, more preferably 25 (w/w) or less, even more preferably 20 (w/w) or less, from the viewpoint of a concentration load. Such bed volume (BV) falls within the range of preferably from 1 (w/w) to 30 (w/w), more preferably from 2 (w/w) to 25 (w/w), even more preferably from 3 (w/w) to 20 (w/w).

In addition, the feeding rate of the aqueous solvent is preferably 0.1 [hr$^{-1}$] or more, more preferably 0.3 [hr$^{-1}$] or more, even more preferably 0.5 [hr$^{-1}$] or more, and is preferably 20 [hr$^{-1}$] or less, more preferably 10 [hr$^{-1}$] or less, even more preferably 5 [hr$^{-1}$] or less, in terms of space velocity (SV) with respect to the mass of the coffee beans, from the viewpoint of an increase in recovery rate of the chlorogenic acid. Such space velocity (SV) falls within the range of preferably from 0.1 [hr$^{-1}$] to 20 [hr$^{-1}$], more preferably from 0.3 [hr$^{-1}$] to 10 [hr$^{-1}$], even more preferably from 0.5 [hr$^{-1}$] to 5 [hr$^{-1}$].

The chlorogenic acid-containing composition to be brought into contact with the porous adsorbent may be obtained by recovering the extract solution discharged from the column extractor, and may be further subjected to solid-liquid separation usually used in the field of food industry, as required. Examples of the solid-liquid separation include paper filtration, centrifugal separation, and membrane filtration. One thereof may be carried out, or two or more thereof may be appropriately carried out in combination.

When the thus obtained extract solution has solids concentration of from 1.5 mass % to 4.7 mass %, the extract solution may be used as it is as the chlorogenic acid-containing composition according to the present invention to be brought into contact with the porous adsorbent. For example, in the case where the extract solution is continuously discharged and the solids concentration varies at each time point as in the column extraction, when the continuously discharged extract solution has solids concentration of from 1.5% to 4.7% as an average value, the extract solution may be used as it is as the chlorogenic acid-containing composition according to the present invention to be brought into contact with the porous adsorbent.

In addition, the extract solution may be concentrated or diluted to adjust its concentration. For example, the extract solution may, when having solids concentration of more than 4.7 mass %, be diluted to 4.7 mass % or less, or may, when having solids concentration of less than 1.5 mass %, be concentrated to 1.5 mass % or more, to be brought into contact with the porous adsorbent as the chlorogenic acid-containing composition according to the present invention. In addition, for example, even when the solids concentration of the extract solution is 4.7 mass % or less, the extract solution may be diluted after being concentrated so as to have a desired solids concentration. As a concentration method, there are given, for example, a normal-pressure concentration method, a reduced-pressure concentration method, and a membrane concentration method. Concentration conditions may be appropriately selected depending on the concentration method.

[Contact Step]

In the present invention, the production method comprises a contact step of bringing the above-mentioned chlorogenic acid-containing composition into contact with a porous adsorbent.

At least one selected from the group consisting of activated carbon, activated clay, and acid clay may be used as the porous adsorbent. Of those, activated carbon is preferred from the viewpoints of the caffeine-selective removing property and the treatable solids amount with respect to a unit weight of the porous adsorbent, and the viewpoint of allowing the taste and flavor of coffee to remain.

A raw material from which the activated carbon is derived is, for example, sawdust, coal, or coconut shell. Of those, coconut shell activated carbon derived from coconut shell is preferred. In addition, activated carbon that has been activated with a gas, such as steam, is preferably used.

The pore radius of the activated carbon is preferably 1.0 nm or less, more preferably 0.7 nm or less, even more preferably 0.5 nm or less, and is preferably 0.1 nm or more, more preferably 0.2 nm or more, even more preferably 0.25 nm or more, from the viewpoint of a reduction in caffeine. Such pore radius falls within the range of preferably from 0.1 nm to 1.0 nm, more preferably from 0.2 nm to 0.7 nm, more preferably from 0.2 nm to 0.5 nm, even more preferably from 0.25 nm to 0.5 nm. The term "pore radius" as used herein refers to the value of a pore radius showing a peak top of a pore distribution curve obtained by the MP method.

In addition, the average particle size of the activated carbon is preferably 0.01 mm or more, more preferably 0.05 mm or more, even more preferably 0.10 mm or more, and is preferably 2.0 mm or less, more preferably 1.5 mm or less, even more preferably 1.0 mm or less, from the viewpoint of a reduction in caffeine. Such average particle size falls within the range of preferably from 0.01 mm to 2.0 mm, more preferably from 0.05 mm to 1.5 mm, even more preferably from 0.10 mm to 1.0 mm. The term "average particle size of the activated carbon" as used herein means a mass-average particle size as determined by determining a particle size on the basis of the section 6.3 of JIS K1474, and then determining a particle size distribution on the basis of the section 6.4 thereof, followed by calculation based on b) 7) of the section.

The acid clay and the activated clay both contain, as general chemical components, $SiO_2$, $Al_2O_3$, $Fe_2O_3$, $CaO$, $MgO$, and the like, and have a $SiO_2/Al_2O_3$ mass ratio of preferably from 3 to 12, more preferably from 4 to 9. In addition, the acid clay or the activated clay preferably has a composition containing 2 mass % to 5 mass % of $Fe_2O_3$, 0 mass % to 1.5 mass % of $CaO$, and 1 mass % to 7 mass % of $MgO$.

The activated clay is a product obtained by treating naturally occurring acid clay (montmorillonite-based clay) with a mineral acid, such as sulfuric acid, and is a compound having a porous structure with a large specific surface area and adsorption capability. It is known that, when the acid clay is further treated with an acid, the specific surface area is changed, to thereby improve its decoloring capacity and change its physical properties.

The specific surface area of the acid clay or the activated clay varies depending on the degree of the acid treatment or the like, and is preferably from 50 m$^2$/g to 350 m$^2$/g. In addition, the acid clay or the activated clay has a pH of preferably from 2.5 to 8, more preferably from 3.6 to 7, as a 5% suspension. For example, a commercially available product, such as MIZUKA ACE #600 (manufactured by Mizusawa Industrial Chemicals, Ltd.), may be used as the acid clay.

The usage amount of the porous adsorbent with respect to the solids of the chlorogenic acid-containing composition is preferably 50 mass % or more, more preferably 80 mass % or more, even more preferably 150 mass % or more, from the viewpoint of a reduction in caffeine, and is preferably 400 mass % or less, more preferably 370 mass % or less, even more preferably 350 mass % or less, from the viewpoint of a yield. The usage amount of the porous adsorbent falls within the range of preferably from 50 mass % to 400 mass %, more preferably from 80 mass % to 370 mass %, even more preferably from 150 mass % to 350 mass %, with respect to the solids of the chlorogenic acid-containing composition.

As a method for the contact with the porous adsorbent, there may be given, for example, a batchwise method and a continuous method. Of those, a continuous method involving continuously passing the chlorogenic acid-containing composition through a column filled with the porous adsorbent is preferred from the viewpoint of production efficiency. In the case of the continuous method, the chlorogenic acid-containing composition may be supplied from the lower part of the column toward the upper part thereof (upflow), or may be supplied from the upper part toward the lower part (downflow), and the supply direction may be appropriately selected.

In the case of the continuous method, a space velocity (SV) with respect to the mass of the porous adsorbent is preferably 0.1 [$h^{-1}$] or more, more preferably 1.0 [$h^{-1}$] or more, even more preferably 5.0 [$h^{-1}$] or more, and is preferably 20 [$h^{-1}$] or less, more preferably 15 [$h^{-1}$] or less, even more preferably 10 [$h^{-1}$] or less. Such space velocity (SV) falls within the range of preferably from 0.1 [$h^{-1}$] to 20 [$h^{-1}$], more preferably from 1.0 [$h^{-1}$] to 15 [$h^{-1}$], even more preferably from 5.0 [$h^{-1}$] to 10 [$h^{-1}$].

In addition, the contact with the porous adsorbent is performed at a temperature of preferably 30° C. or more, more preferably 40° C. or more, more preferably 50° C. or more, even more preferably 60° C. or more, from the viewpoints of the caffeine-selective removing property and the treatable solids amount with respect to a unit weight of the porous adsorbent, and of preferably 150° C. or less, more preferably 120° C. or less, even more preferably 100° C. or less, from the viewpoint of a yield. Such contact temperature falls within the range of preferably from 30° C. to 150° C., more preferably from 40° C. to 120° C., more preferably from 50° C. to 100° C., even more preferably from 60° C. to 100° C.

After the contact with the porous adsorbent, the liquid having been treated with the porous adsorbent may be subjected to solid-liquid separation. Examples of the solid-liquid separation include the same examples as described above. One thereof may be carried out, or two or more thereof may be carried out in combination.

The purified chlorogenic acid-containing composition of the present invention may be obtained by recovering the liquid having been treated with the porous adsorbent. The purified chlorogenic acid-containing composition may be in any of various forms, such as a liquid, a slurry, a semisolid, and a solid. In addition, the purified chlorogenic acid-containing composition is preferably further concentrated in order to increase the solids concentration. As in the foregoing, as a concentration method, there are given, for example, a normal-pressure concentration method, a reduced-pressure concentration method, and a membrane concentration method. Further, when a solid is preferred as the product form of the purified chlorogenic acid-containing composition, the purified chlorogenic acid-containing composition may be dried by a known method, such as spray drying or freeze drying.

The content of a chlorogenic acid in the solids of the purified chlorogenic acid-containing composition obtained by the production method of the present invention is preferably from 10 mass to 80 mass %, more preferably from 25 mass % to 75 mass %, even more preferably from 40 mass % to 70 mass %, from the viewpoint of taste and flavor.

The present invention further discloses the following production method regarding the above-mentioned embodiment.

<1>
A method of producing a purified chlorogenic acid-containing composition, comprising a step of bringing a chlorogenic acid-containing composition having solids concentration of from 1.5 mass % to 4.7 mass % and a mass ratio of "caffeine/chlorogenic acid of 5 or less into contact with a porous adsorbent.

<2>
The method of producing a purified chlorogenic acid-containing composition according to the above-mentioned item <1>, wherein the chlorogenic acid comprises preferably at least one selected from the group consisting of 3-caffeoylquinic acid, 4-caffeoylquinic acid, 5-caffeoylquinic acid, 3-feruloylquinic acid, 4-feruloylquinic acid, and 5-feruloylquinic acid, more preferably all of the six kinds.

<3>
The method of producing a purified chlorogenic acid-containing composition according to the above-mentioned item <1> or <2>, wherein the solids concentration of the chlorogenic acid-containing composition is preferably from 1.5 mass % to 4.5 mass %, more preferably from 1.6 mass % to 4.0 mass %, even more preferably from 1.7 mass % to 3.5 mass %.

<4>
The method of producing a purified chlorogenic acid-containing composition according to any one of the above-mentioned items <1> to <3>, wherein the mass ratio of caffeine/chlorogenic acid in the chlorogenic acid-containing composition is preferably from 0.001 to 2.5, more preferably from 0.005 to 1, even more preferably from 0.01 to 0.4.

<5>
The method of producing a purified chlorogenic acid-containing composition according to any one of the above-mentioned items <1> to <4>, wherein the chlorogenic acid-containing composition preferably has solids concentration of from 1.5 mass to 4.5 mass %, and a mass ratio of caffeine/chlorogenic acid of from 0.01 to 0.4.

<6>
The method of producing a purified chlorogenic acid-containing composition according to any one of the above-mentioned items <1> to <5>, wherein the chlorogenic acid-containing composition is preferably in a liquid, slurry, semisolid, or solid form, and may be concentrated.

<7>
The method of producing a purified chlorogenic acid-containing composition according to any one of the above-mentioned items <1> to <6>, wherein the porous adsorbent comprises preferably at least one selected from the group consisting of activated carbon, activated clay, and acid clay, more preferably activated carbon.

<8>
The method of producing a purified chlorogenic acid-containing composition according to any one of the above-mentioned items <1> to <7>, wherein a method for the contact with the porous adsorbent is preferably a batchwise method or a continuous method, more preferably a continuous method.

<9>
The method of producing a purified chlorogenic acid-containing composition according to any one of the above-mentioned items <1> to <8>, wherein the contact with the porous adsorbent is performed at a temperature of preferably from 30° C. to 150° C., more preferably from 40° C. to 120° C., more preferably from 50° C. to 100° C., even more preferably from 60° C. to 100° C.

<10>
The method of producing a purified chlorogenic acid-containing composition according to any one of the above-mentioned items <1> to <9>, wherein a usage amount of the porous adsorbent is preferably from 50 mass % to 400 mass %, more preferably from 80 mass % to 370 mass %, even more preferably from 150 mass % to 350 mass %, with respect to the solids of the chlorogenic acid-containing composition.

<11>

The method of producing a purified chlorogenic acid-containing composition according to any one of the above-mentioned items <1> to <10>, preferably further comprising a step of subjecting a solution treated with the porous adsorbent to solid-liquid separation after the contact with the porous adsorbent.

<12>

The method of producing a purified chlorogenic acid-containing composition according to the above-mentioned item <11>, wherein the solid-liquid separation preferably comprises one or two or more selected from the group consisting of paper filtration, centrifugal separation, and membrane filtration.

<13>

The method of producing a purified chlorogenic acid-containing composition according to any one of the above-mentioned items <1> to <12>, wherein the purified chlorogenic acid-containing composition is preferably in a liquid, slurry, semisolid, or solid form.

<14>

The method of producing a purified chlorogenic acid-containing composition according to any one of the above-mentioned items <1> to <13>, wherein the purified chlorogenic acid-containing composition has a content of the chlorogenic acid in solids of preferably from 10 mass % to 80 mass %, more preferably from 25 mass to 75 mass %, even more preferably from 40 mass % to 70 mass %.

EXAMPLES

1. Analysis of Chlorogenic Acid (CGA) and Caffeine (Caf) (Analyzer)

An UPLC (manufactured by Nihon Waters K.K.) was used. The model numbers of component units in the analyzer are as follows:

Apparatus: Waters ACQUITY UPLC
Column: ACQUITY UPLC™ C18, 2.1×100 nm, 1.7 μm
Detector: photodiode array detector (PDA)
(Analysis Conditions)
Sample injection volume: 10 μL
Flow rate: 1.0 mL/min
Ultraviolet absorption spectrophotometer detection wavelengths: 325 nm (chlorogenic acid) and 270 nm (caffeine)
Eluent A: A solution of acetonitrile diluted with water to an acetonitrile concentration of 5 (V/V) %, the solution containing 0.05 M acetic acid, 0.1 mM 1-hydroxyethane-1,1-diphosphonic acid, and 10 mM sodium acetate
Eluent B: Acetonitrile Concentration Gradient Conditions (Vol %)

| Time | Eluent A | Eluent B |
|---|---|---|
| 0.0 min | 100% | 0% |
| 2.5 min | 100% | 0% |
| 3.5 min | 95% | 5% |
| 5.0 min | 95% | 5% |
| 6.0 min | 92% | 8% |

-continued

| Time | Eluent A | Eluent B |
|---|---|---|
| 16.0 min | 92% | 8% |
| 16.5 min | 10% | 90% |
| 19.0 min | 100% | 0% |
| 22.0 min | 100% | 0% |

(1) Retention Time of Chlorogenic Acid (CGA)
3-Caffeoylquinic acid (3-CQA): 1.3 min
5-Caffeoylquinic acid (5-CQA): 2.1 min
4-Caffeoylquinic acid (4-CQA): 2.9 min
3-Feruloylquinic acid (3-FQA): 3.3 min.
5-Feruloylquinic acid (5-FQA): 5.0 min
4-Feruloylquinic acid (4-FQA): 5.4 min 5-CQA was used as a standard substance to determine the content (mass %) of the chlorogenic acid based on the area determined in the foregoing.

(2) Retention Time of Caffeine (Caf)
Caffeine: 4.8 min

Reagent caffeine was used as a standard substance to determine the content (mass %) of caffeine based on the area % determined in the foregoing.

2. Measurement of L Value of Roasted Coffee Beans

A sample was ground to an average particle size of 0.3 mm and then subjected to measurement using a colorimeter (manufactured by Nippon Denshoku Industries Co., Ltd., Spectrophotometer 5E2000).

3. Measurement of Average Particle Size of Ground Coffee Beans

Ten ground coffee beans were randomly taken, each of the beans was measured for its long diameter, short diameter, and intermediate diameter with a vernier caliper, and the average of the measured values was defined as an average particle size. As used herein, the term "long diameter" refers to the length of the longest portion in an observation surface of a ground coffee bean, the term "short diameter" refers to the length of the longest portion in the direction perpendicular to the long diameter, and the term "intermediate diameter" refers to the length of the longest portion in the vertical direction of the observation surface. However, when such value was 2 mm or less, the "average particle size" was determined as a particle size corresponding to 50% ($d_{50}$) in a cumulative particle size distribution curve on a volume basis obtained by dry measurement with a laser diffraction/scattering particle size distribution analyzer (LS13 320, manufactured by Beckman Coulter) utilizing the dependence of a diffracted/scattered light intensity pattern on the size of a particle.

4. Calculation of Change Ratio of Caffeine/Chlorogenic Acid Before and after Purification The change ratio of caffeine/chlorogenic acid before and after purification was calculated by the following equation. The change ratio of caffeine/chlorogenic acid before and after purification is an indicator of whether a chlorogenic acid can be selectively recovered even when caffeine is removed through porous adsorbent treatment.

$$\text{Change ratio of caffeine/chlorogenic acid (\%)} = 100 - (C/D)/(E/F) \times 100$$

In the equation, C represents the mass (g) of caffeine after contact with a porous adsorbent, D represents the mass (g) of the chlorogenic acid after contact with the porous adsorbent, E represents the mass (g) of caffeine before contact with the porous adsorbent, and F represents the mass (g) of the chlorogenic acid before contact with the porous adsorbent. The values of C and D are values as determined by analyzing a collected solution obtained by treating 1 g of solids with respect to 1 g of the porous adsorbent.

5. Calculation of Treatable Solids Amount of Chlorogenic Acid-Containing Material with Respect to Unit Amount of Porous Adsorbent The solids amount of a chlorogenic acid-containing composition before purification with respect to a unit amount of a porous adsorbent, the amount being treatable by the time the "caffeine/chlorogenic acid" value of a collected solution obtained by purification became 0.1, was calculated by the following equation.

Treatable solids amount of chlorogenic acid-containing material with respect to unit amount of porous adsorbent=G×H/I In the equation, G represents the mass (g) of the recovered solution (having a "caffeine/chlorogenic acid" value of 0.1), H represents the solids concentration (mass %) of the chlorogenic acid-containing composition before contact with the porous adsorbent, and I represents the mass (g) of the porous adsorbent used.

Production Example 1

Production of Chlorogenic Acid-Containing Composition A 45 g of unground green robusta coffee beans were charged into a column having a volume of 208 cm$^3$. Next, 3 parts by mass of hot water at 80° C. was supplied to the column from a supply valve in a lower part of the column at a feeding rate of SV=2 [hr$^{-1}$]. Next, after the supply valve in the lower part of the column had been closed, hot water at 80° C. was supplied from a shower nozzle in an upper part under the conditions of a feeding rate (SV) of 2 [hr$^{-3}$] and a bed volume (BV) of 12 (w/w), and simultaneously, a discharge valve in the lower part of the column was opened to continuously take out a "chlorogenic acid-containing composition". The resultant chlorogenic acid-containing composition A had a "caffeine/chlorogenic acid" mass ratio of 0.32.

Production Example 2

Production of Chlorogenic Acid-Containing Composition B 45 g of unground roasted robusta coffee beans (L value: 35) were charged into a column having a volume of 208 cm$^3$. Next, 3 parts by mass of hot water at 80° C. was supplied to the column from a supply valve in a lower part of the column at a feeding rate of SV=2 [hr$^{-1}$]. Next, after the supply valve in the lower part of the column had been closed, hot water at 80° C. was supplied from a shower nozzle in an upper part under the conditions of a feeding rate (SV) of 2 [hr$^{-1}$] and a bed volume (BV) of 12 (w/w), and simultaneously, a discharge valve in the lower part of the column was opened to continuously take out a "chlorogenic acid-containing composition". The resultant chlorogenic acid-containing composition B had a "caffeine/chlorogenic acid" mass ratio of 0.50.

Production Example 3

Production of Chlorogenic Acid-Containing Composition C 45 g of unground roasted robusta coffee beans (L value: 19) were charged into a column having a volume of 208 cm$^3$. Next, 3 parts by mass of hot water at 80° C. was supplied to the column from a supply valve in a lower part of the column at a feeding rate of SV=2 [hr$^{-1}$]. Next, after the supply valve in the lower part of the column had been closed, hot water at 80° C. was supplied from a shower nozzle in an upper part under the conditions of a feeding rate (SV) of 2 [hr$^{-1}$] and a bed volume (BV) of 12 (w/w), and simultaneously, a discharge valve in the lower part of the column was opened to continuously take out a "chlorogenic acid-containing composition". The resultant chlorogenic acid-containing composition C had a "caffeine/chlorogenic acid" mass ratio of 10.

Example 1

The chlorogenic acid-containing composition A obtained in Production Example 1 was concentrated under reduced pressure with an evaporator to provide a concentrate. Next, the concentrate was diluted with ion-exchanged water to provide a chlorogenic acid-containing composition having solids concentration of 1.7 mass %. Next, the chlorogenic acid-containing composition was fed to a column filled with 10.4 g of activated carbon (manufactured by Kuraray Chemical Co., Ltd., Kuraray Coal GW) at a feeding rate of a feeding rate (SV) of 7 [hr$^{-1}$] in an upflow at a constant temperature of 25° C., and the liquid having been treated with the activated carbon was analyzed.

Example 2

The chlorogenic acid-containing composition A obtained in Production Example 1 was concentrated and diluted in the same manner as in Example 1 to provide a chlorogenic acid-containing composition having solids concentration of 2.6 mass %. Next, the chlorogenic acid-containing composition was treated with activated carbon in the same manner as in Example 1 to provide a purified chlorogenic acid-containing composition. The resultant purified chlorogenic acid-containing composition was analyzed.

Example 3

The chlorogenic acid-containing composition A obtained in Production Example 1 was concentrated and diluted in the same manner as in Example 1 to provide a chlorogenic acid-containing composition having solids concentration of 3.0 mass %. Next, the chlorogenic acid-containing composition was treated with activated carbon in the same manner as in Example 1 to provide a purified chlorogenic acid-containing composition. The resultant purified chlorogenic acid-containing composition was analyzed.

Example 4

The chlorogenic acid-containing composition A obtained in Production Example 1 was concentrated and diluted in the same manner as in Example 1 to provide a chlorogenic acid-containing composition having solids concentration of 4.4 mass %. Next, the chlorogenic acid-containing composition was treated with activated carbon in the same manner as in Example 1 to provide a purified chlorogenic acid-containing composition. The resultant purified chlorogenic acid-containing composition was analyzed.

Comparative Example 1

The chlorogenic acid-containing composition A obtained in Production Example 1 was concentrated and diluted in the same manner as in Example 1 to provide a chlorogenic acid-containing composition having solids concentration of 5.0 mass %. Next, the chlorogenic acid-containing composition was treated with activated carbon in the same manner as in Example 1 to provide a purified chlorogenic acid-containing composition. The resultant purified chlorogenic acid-containing composition was analyzed.

Example 5

A purified chlorogenic acid-containing composition was obtained in the same manner as in Example 1 except that the temperature at which the chlorogenic acid-containing composition was fed to the column filled with activated carbon was changed to 50° C. The resultant purified chlorogenic acid-containing composition was analyzed.

Example 6

A purified chlorogenic acid-containing composition was obtained in the same manner as in Example 1 except that the temperature at which the chlorogenic acid-containing composition was fed to the column filled with activated carbon was changed to 85° C. The resultant purified chlorogenic acid-containing composition was analyzed.

Example 7

The chlorogenic acid-containing composition B obtained in Production Example 2 was concentrated and diluted in the same manner as in Example 1 to provide a chlorogenic acid-containing composition having solids concentration of 1.8 mass %. Next, the chlorogenic acid-containing composition was treated with activated carbon in the same manner as in Example 1 to provide a purified chlorogenic acid-containing composition. The resultant purified chlorogenic acid-containing composition was analyzed.

Example 8

The chlorogenic acid-containing composition A obtained in Production Example 1 was concentrated and diluted in the same manner as in Example 1 to provide a chlorogenic acid-containing composition having solids concentration of 1.7 mass %. Next, 150 g of the chlorogenic acid-containing composition and 1.3 g of acid clay (MIZUKA ACE #600, manufactured by Mizusawa Industrial Chemicals, Ltd.) were brought into contact with each other at 25° C. for 180 minutes to provide a clay adsorption liquid. The clay adsorption liquid was filtered through a 0.2 μm filter to provide a purified chlorogenic acid-containing composition. The resultant purified chlorogenic acid-containing composition was analyzed.

Comparative Example 2

The chlorogenic acid-containing composition C obtained in Production Example 3 was concentrated and diluted in the same manner as in Example 1 to provide a chlorogenic acid-containing composition having solids concentration of 1.8 mass %. Next, the chlorogenic acid-containing composition was treated with activated carbon in the same manner as in Example 1 to provide a purified chlorogenic acid-containing composition. The resultant purified chlorogenic acid-containing composition was analyzed.

TABLE 1

| | | Example 1 | Example 2 | Example 3 | Example 4 | Comparative Example 1 | Example 5 | Example 6 | Example 7 | Comparative Example 2 | Example 8 |
|---|---|---|---|---|---|---|---|---|---|---|---|
| Coffee beans | Green beans or roasted beans (L value) | Green beans | Green beans | Green beans | Green beans | Green beans | Green beans | Green beans | Roasted beans L35 | Roasted beans L19 | Green beans |
| | Particle size | Unground | Unground | Unground | Unground | Unground | Unground | Unground | Unground | Unground | Unground |
| Chlorogenic acid-containing composition | Solids concentration [%] | 1.7 | 2.6 | 3.0 | 4.4 | 5.0 | 1.7 | 1.7 | 1.8 | 1.8 | 1.7 |
| | Caffeine/Chlorogenic acid-containing composition [—] | 0.32 | 0.32 | 0.32 | 0.32 | 0.32 | 0.32 | 0.32 | 0.50 | 10 | 0.32 |
| Adsorbent | Kind | Activated carbon | Activated carbon | Activated carbon | Activated carbon | Activated carbon | Activated carbon | Activated carbon | Activated carbon | Activated carbon | Clay |
| Adsorbent treatment conditions | Temperature [° C.] | 25 | 25 | 25 | 25 | 25 | 50 | 85 | 25 | 25 | 25 |
| Evaluation 1 | Change ratio of caffeine/chlorogenic acid [%] | 74 | 64 | 64 | 50 | 45 | 89 | 94 | 59 | 62 | 56 |
| Evaluation 2 | Treatable solids amount [g-solids/g-adsorbent] | 1.2 | 0.90 | 0.85 | 0.47 | 0.29 | >1.3 | >1.3 | 0.40 | 0.01 | 0.77 |

Evaluation 1: Treatment of 1 g of solids with respect to 1 g of adsorbent
Evaluation 2: Caffeine/chlorogenic acid of collected solution = 0.1

It found from Table 1 that, when a chlorogenic acid-containing composition having solids concentration of from 1.5 mass % to 4.7 mass is brought into contact with a porous adsorbent, there can be produced a purified chlorogenic acid-containing composition in which a selective reduction in caffeine is achieved.

It also found that, when the chlorogenic acid-containing composition is brought into contact with the porous adsorbent at 25° C. or more, the purified chlorogenic acid-containing composition can be produced with a small amount of the porous adsorbent while achieving a selective reduction in caffeine.

It also found that, when a chlorogenic acid-containing composition having a "caffeine/chlorogenic acid" mass ratio of 5 or less is brought into contact with the porous adsorbent, the purified chlorogenic acid-containing composition can be produced with a small amount of the porous adsorbent while achieving a reduction in caffeine.

The invention claimed is:

1. A method of producing a purified chlorogenic acid-containing composition, comprising:
    providing a chlorogenic acid-containing composition comprising chlorogenic acid and caffeine, wherein the chlorogenic acid-containing composition has a solids concentration of from 1.5 mass % to 4.7 mass % and a mass ratio of caffeine to chlorogenic acid is from 0.001 to 0.4; and
    contacting the chlorogenic acid-containing composition with a porous adsorbent at a temperature of from 50° C. to 100° C.;
    wherein the change ratio of caffeine to chlorogenic acid before and after purification is 89% or more, wherein the change ratio of caffeine to chlorogenic acid (%)=100−(C/D)/(E/F)×100, wherein C represents the mass of caffeine after contact with the porous adsorbent, D represents the mass of the chlorogenic acid after contact with the porous adsorbent, E represents the mass of caffeine before contact with the porous adsorbent, and F represents the mass of the chlorogenic acid before contact with the porous adsorbent.

2. The method of producing a purified chlorogenic acid-containing composition according to claim 1, wherein the porous adsorbent comprises activated carbon.

3. The method of producing a purified chlorogenic acid-containing composition according to claim 2, wherein a pore radius of the activated carbon is from 0.1 nm to 1.0 nm.

4. The method of producing a purified chlorogenic acid-containing composition according to claim 2, wherein an average particle size of the activated carbon is from 0.01 mm to 2.0 mm.

5. The method of producing a purified chlorogenic acid-containing composition according to claim 1, wherein the method of contacting the chlorogenic acid-containing composition with the porous adsorbent is a continuous method.

6. The method of producing a purified chlorogenic acid-containing composition according to claim 1, wherein the porous adsorbent is used in an amount from 50 mass % to 400 mass % with respect to the solids concentration of the chlorogenic acid-containing composition.

7. The method of producing a purified chlorogenic acid-containing composition according to claim 1, further comprising a step of subjecting a solution treated with the porous adsorbent to solid-liquid separation after the contact with the porous adsorbent.

8. The method of producing a purified chlorogenic acid-containing composition according to claim 7, wherein the solid-liquid separation comprises one or two or more selected from the group consisting of paper filtration, centrifugal separation and membrane filtration.

9. The method of producing a purified chlorogenic acid-containing composition according to claim 1, further comprising, before the contact step, a step of obtaining the chlorogenic acid-containing composition having solids concentration of from 1.5 mass % to 4.7 mass % and a mass ratio of caffeine to chlorogenic acid is from 0.001 to 0.4 through a step comprising an extraction step of subjecting at least one selected from the group consisting of green coffee beans, decaffeinated green coffee beans, roasted coffee beans having an L value of 30 or more, and decaffeinated roasted coffee beans having an L value of 25 or more, to column extraction using an aqueous solvent.

10. The method of producing a purified chlorogenic acid-containing composition according to claim 9, wherein an extraction temperature in the extraction step is from 75° C. to 98° C.

11. The method of producing a purified chlorogenic acid-containing composition according to claim 9, wherein the aqueous solvent comprises water.

12. The method of producing a purified chlorogenic acid-containing composition according to claim 1, wherein the chlorogenic acid is selectively recovered.

13. The method of producing a purified chlorogenic acid-containing composition according to claim 12, wherein caffeine is removed through a porous adsorbent treatment.

14. The method of producing a purified chlorogenic acid-containing composition according to claim 1, wherein a value of G×H/I is >1.3, wherein G represents a mass of the recovered solution, H represents the solids concentration (mass %) of the chlorogenic acid-containing composition before contact with the porous adsorbent, and I represents the mass (g) of the porous adsorbent used.

15. The method of producing a purified chlorogenic acid-containing composition according to claim 1, wherein the porous adsorbent is used in an amount from 80 mass % to 370 mass % with respect to the solids concentration of the chlorogenic acid-containing composition.

16. The method of producing a purified chlorogenic acid-containing composition according to claim 1, wherein the porous adsorbent is used in an amount from 150 mass % to 350 mass % with respect to the solids concentration of the chlorogenic acid-containing composition.

* * * * *